United States Patent
Tabeie (12)

(10) Patent No.: US 10,219,788 B2
(45) Date of Patent: Mar. 5, 2019

(54) STRING PHANTOM WITH FOUR INDEPENDENT PARAMETERS FOR EVALUATION OF DOPPLER ULTRASONOGRAPHY INSTRUMENTS

(71) Applicant: Faraj Tabeie, Tehran (IR)

(72) Inventor: Faraj Tabeie, Tehran (IR)

( * ) Notice: Subject to any disclaimer, the term of this patent is extended or adjusted under 35 U.S.C. 154(b) by 0 days.

(21) Appl. No.: 15/853,765

(22) Filed: Dec. 23, 2017

(65) Prior Publication Data

US 2018/0116639 A1    May 3, 2018

(51) Int. Cl.
| | |
|---|---|
| *A61B 8/00* | (2006.01) |
| *A61B 8/08* | (2006.01) |
| *A61B 8/06* | (2006.01) |

(52) U.S. Cl.
CPC ............. *A61B 8/587* (2013.01); *A61B 8/488* (2013.01); *A61B 8/06* (2013.01); *A61B 8/4444* (2013.01)

(58) Field of Classification Search
None
See application file for complete search history.

(56) References Cited

U.S. PATENT DOCUMENTS

| | | | | |
|---|---|---|---|---|
| 2009/0301539 | A1* | 12/2009 | Watts | F24J 2/42 136/201 |
| 2012/0253196 | A1* | 10/2012 | Nagata | A61B 8/5292 600/443 |
| 2014/0371594 | A1* | 12/2014 | Flynn | G01S 15/8984 600/454 |
| 2016/0166237 | A1* | 6/2016 | Yoshiara | A61B 8/5207 600/443 |

FOREIGN PATENT DOCUMENTS

CN        204065134 U    * 12/2014

* cited by examiner

*Primary Examiner* — Andre J Allen
(74) *Attorney, Agent, or Firm* — Azadeh Saidi

(57) ABSTRACT

Doppler ultrasound systems are valuable diagnostic tool for investigation of vascular blood flow pattern and velocity. Error in blood velocity measurements made by doppler instruments will cause probable misdiagnosis in clinical practice. There are different phantom designs for evaluation of the performance and QC of doppler ultrasonography systems. Among different phantom designs the string phantom because of their ability to precise calculation of target velocity were widely used by different investigators. Generally this type of phantom consists of a moving string with known velocity as a target inside a water tank to mimic blood flow inside the vessels of the body. We designed a new string phantom with three dependently adjustable parameters including target velocity, target angle and target depth.

14 Claims, 5 Drawing Sheets

STRING PHANTOM WITH FOUR INDEPENDENT PARAMETERS FOR EVALUATION OF DOPPLER ULTRASONOGRAPHY INSTRUMENTS

BACKGROUND OF INVENTION

Doppler ultrasound systems are valuable diagnostic tools for investigation of vascular blood flow pattern and velocity. Error in blood velocity measurements made by Doppler instruments will cause probable misdiagnosis in clinical practice.

There are different phantom designs for evaluation of the performance and QC of Doppler Ultrasonography systems and the string phantoms were widely used because of their ability to precise calculation of target velocity.

String phantom consists of a moving string with known velocity as a target inside a water tank to mimic blood flow inside the vessels of the body.

There are several parameters defining the position of target inside the water tank in relation to the ultrasound beam. These parameters are target velocity, target angle and target depth.

All string phantoms had three main variable parameters of target angle, target depth and target velocity but only the target velocity is independent and hence target angle and target depth were not independent.

During procedure of QC of Doppler ultrasonography instruments it is necessary to alter the target depth and target angle by phantom. When the operator desires to choose different target angles for a constant value of target depth, altering the target angle will alter the target depth and it is time consuming.

Therefore it would be desirable to eliminate the above mentioned drawback in Doppler ultrasonography phantoms and introduce a phantom with independent parameters.

SUMMARY OF THE INVENTION

The main purpose of this invention is to introduce a phantom to reduce time coarse of quality control of Doppler ultrasonography instruments This invention is a new string phantom with four independent parameters including target velocity, target depth, target angle and target lateral distance for quality control of Doppler ultrasonography systems.

We designed a new string phantom with four independently adjustable parameters including target velocity, target angle and target depth and target lateral distance.

The ability of altering the lateral target in relation to ultrasound beam is a another novel aspect of this phantom that allows precise alignment of target to ultrasound beam.

By considering the above mentioned purpose we designed a new ultrasonography Doppler phantom with two main innovations:

First, we introduce one more variable parameter of lateral target distance. Operator would be able to alter the lateral target in relation to ultrasound beam that allows precise alignment of target to ultrasound beam.

Second, this phantom has four independently variable parameters including target velocity, target angle, target depth and target lateral distance. Altering one of these parameters will not influence the other three parameters.

BRIEF DESCRIPTION OF DRAWINGS AND FIGURES

FIG. 1, shows the whole phantom system consisting of four main sections

FIG. 2, indicates the details of the water tank

FIG. 3, indicates the probe holder device

FIG. 4, indicates the probe holder device attached to the tank in its position

DETAILED DESCRIPTION OF SPECIFICATION AND DRAWINGS

This phantom mimics the flow of blood inside the vessels of the body. A rubber string moves in a closed loop quadratic track inside a water filled tank 1. Moving string simulates blood stream with known velocity and water simulates the stationary tissues surrounding the blood stream.

Figure 1:
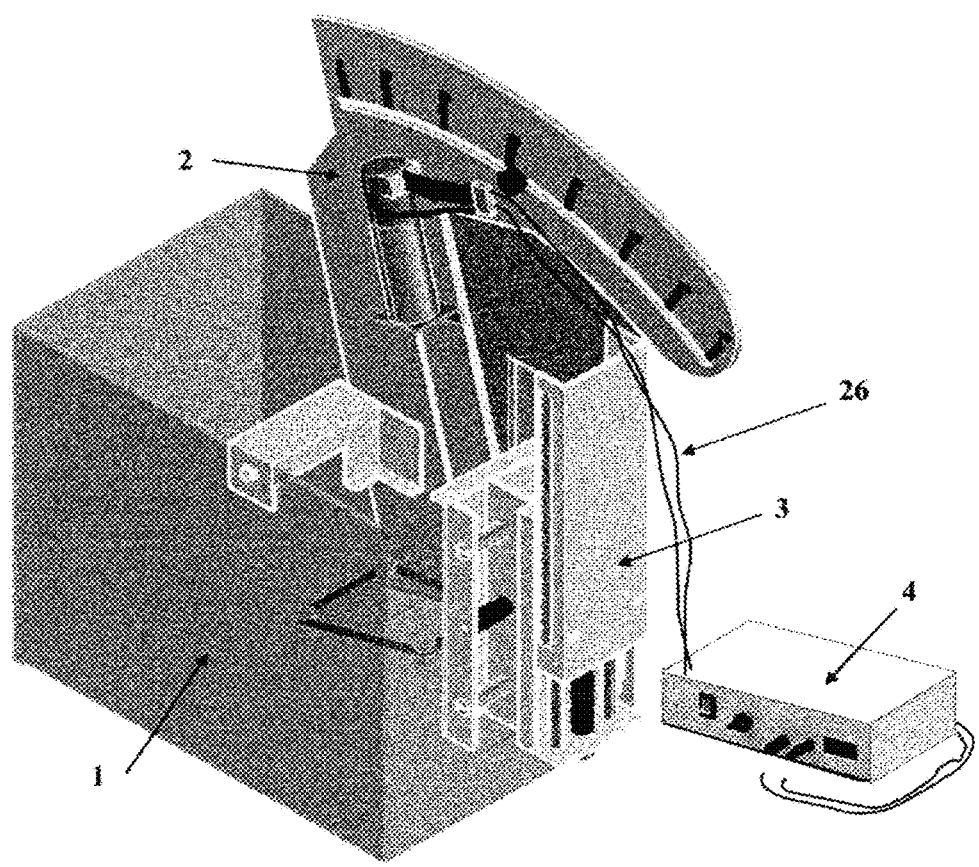

The whole phantom system consisting of four main sections of water tank, X-Y positioning device, target assembly and target velocity control unit as shown in FIG. 1.

The phantom system consisting of four main sections:
1—Water tank.
2—X-Y positioning device that moves the target in X-Y coordinates.
3—Target assembly which holds moving target driven by dc servo motor 15.
4—Target velocity control unit that controls speed of moving target driven by dc motor.

Figure 2:
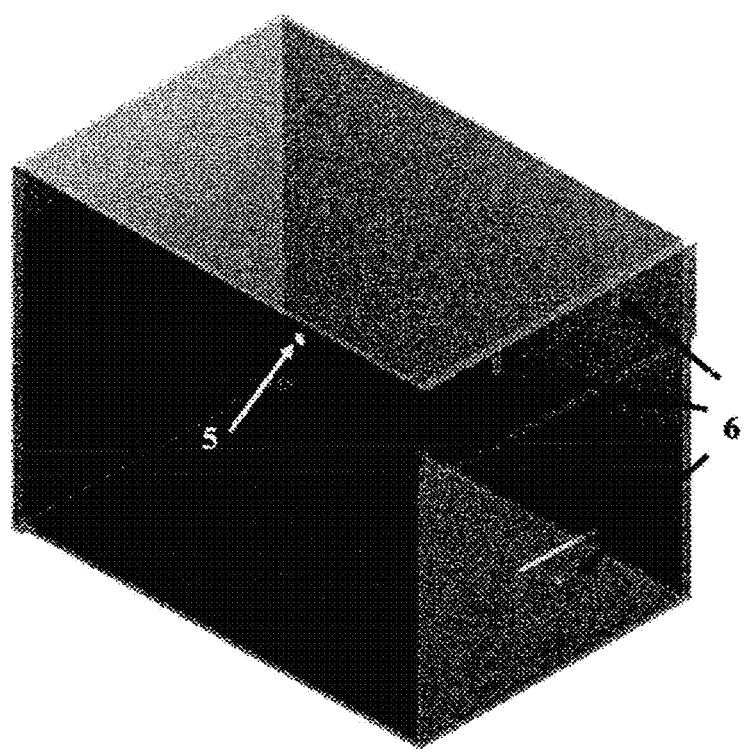

FIG. 2 shows the water tank (1) with dimensions of 32×20×25 cm made from 6 mm thick Plexiglas sheets. There are two positions (5) and (6) provided on the walls of tank (1) for mounting two devices that will be discussed as follows. Probe holder device can be attached by one screw to the wall of tank (1) in position (5). The X-Y positioning device (2) can be attached to the wall of tank (1) by three screws (6).

Figure 3:
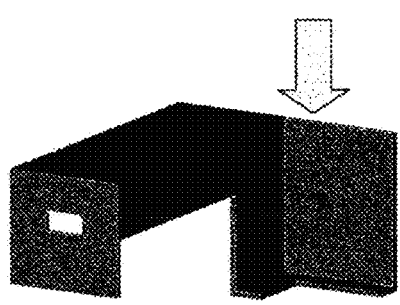

Probe holder device (7) as shown in (FIG. 3) is made from 2 mm thick Aluminum sheet. This device holds the probe in direction perpendicular to water level in tank (1) indicated by arrow in FIG. 3. The ultrasound probe will be fastened by a Velcro strip (not shown) to this device in position indicated by number 5 in FIG. 1 and defines the alignment of the ultrasound beam to the moving target.

Figure 4:
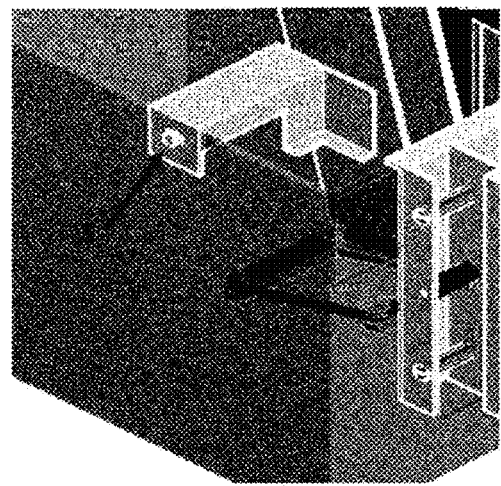

FIG. 4 indicates the probe holder device attached to the tank in its position (5).

Figure 5:
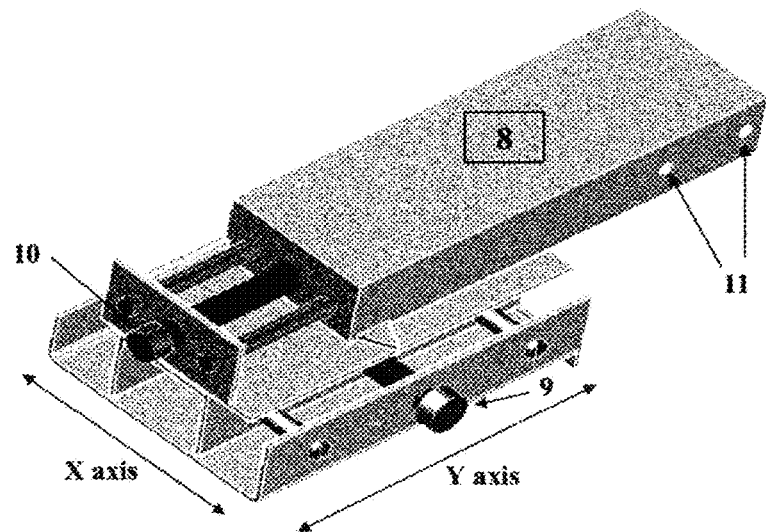
FIG. 5, shows the X-Y positioning device

X-Y positioning device (2) is shown in FIG. 5. This device can adjust the location of moving part (8) in two X and Y axis. Knob (9) sets the position of the moving part in X direction in the range of 0-8 cm. Knob (10) sets the position of the moving part in Y direction in the range of 1-16 cm. So, the depth of target can be set by knob (10) and lateral distance of target can be set by knob (9) in FIG. 5.

The target assembly (3) can be attached to the X-Y positioning device (2) by two screws in position (11).

Figure 6:
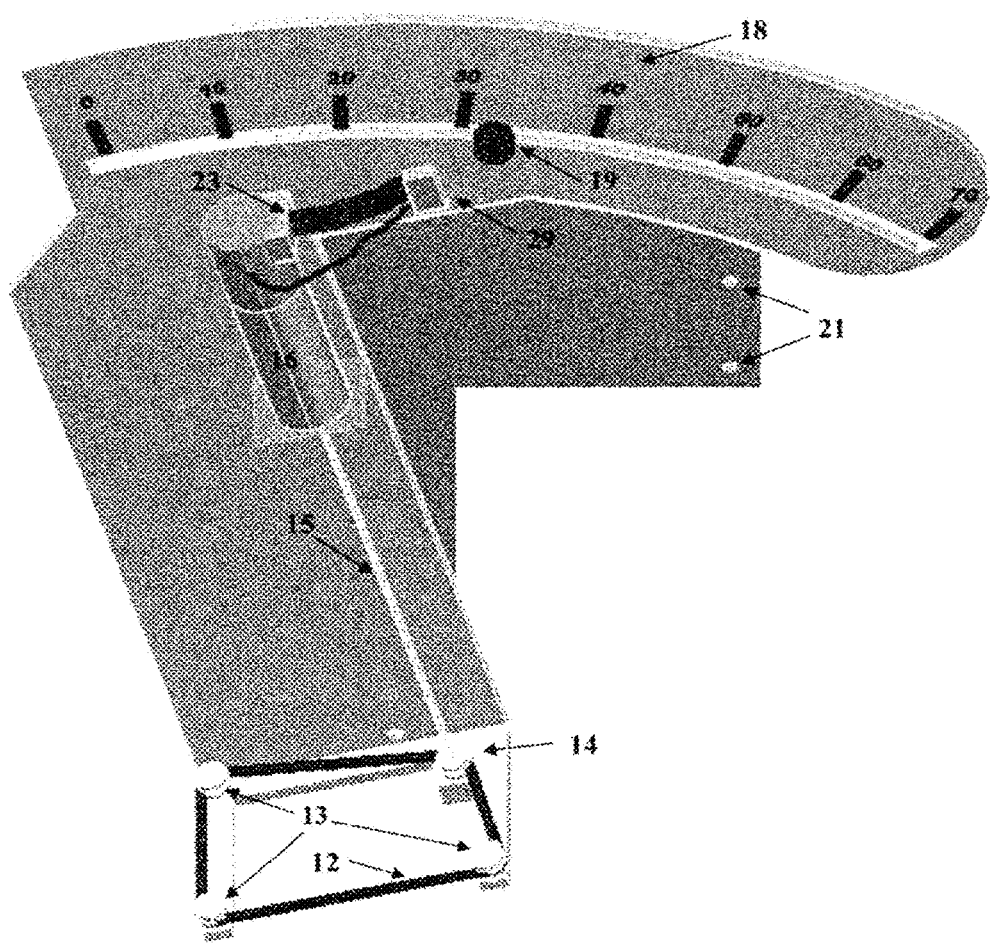
FIG. 6, shows the target assembly
Figure 7:
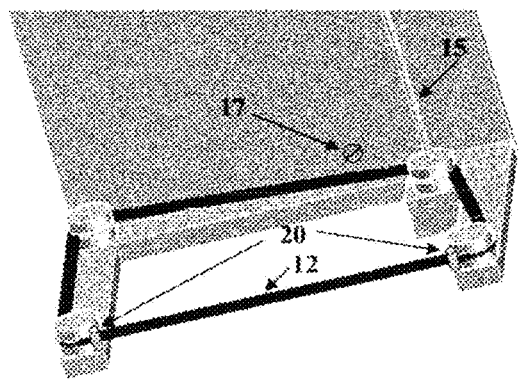
FIG. 7, shows details of the target moving section of target assembly

Target assembly (3) is shown in FIG. 6. An O-ring shaped rubber (12) hold by four pulleys (13) and (14) defines the moving string target for Doppler ultrasonography systems. One of the pulleys (14) is rotated by shaft (15) of dc motor (16) with controlled speed. The details of the moving string target is shown also in FIG. 7. The moving string target (12) can rotate around the point (17) changing its angle to the horizontal axis in the range of 0-65°. The angle of the moving string target can be indicated by the scale on top of the target assembly, (18) that is 25° in FIG. 6. A knob (19) tightens moving string target at the adjusted value of angle. The probe of Doppler ultrasound attaches to the probe holder device (7) directing the ultrasound beam towards the moving string target immersed in the water tank. Two stainless steel pins (20) are mounted so that touching the moving string target to prevent it's vibration during moving by pulleys (13) and (14). The target assembly (3) attaches by two screws (21) to the X-Y positioning device (2) in (FIG. 5).

Figure 8:
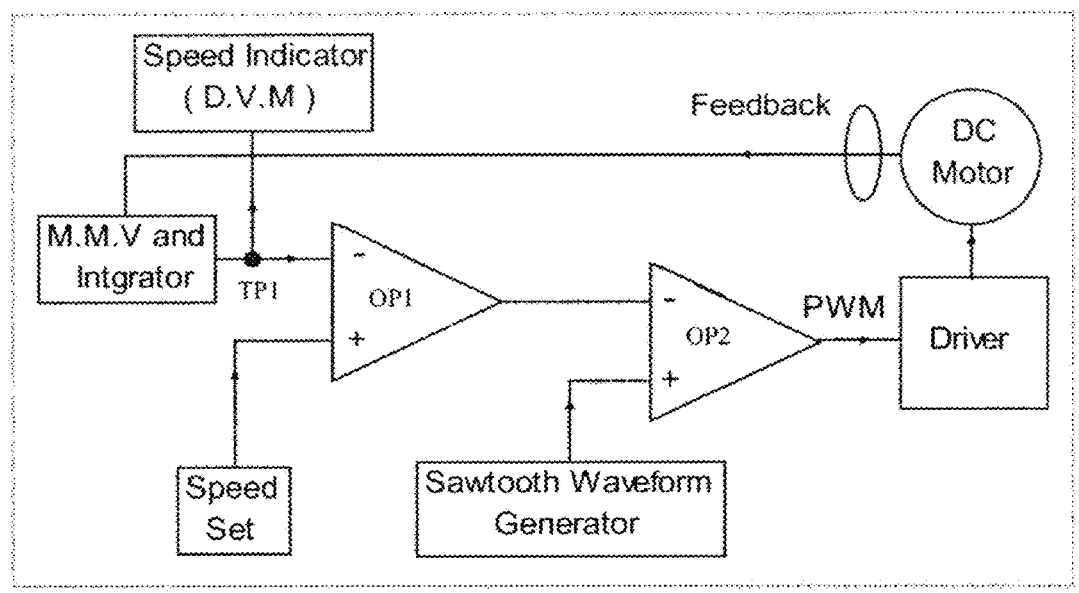
FIG. 8, shows the block diagram of target velocity control unit that employs a proportional closed loop servo control system
Figure 9:
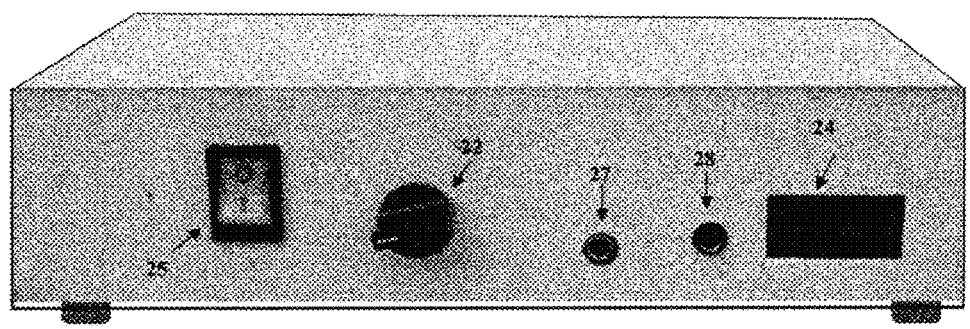
FIG. 9, shows the target velocity control unit

Block diagram of target velocity control (4) is shown in FIG. 8 and the constructed unit is also shown in FIG. 9. The diagram is a closed loop proportional servo control system for deriving the dc motor (15). This system compares the real speed of motor (feedback pulses of motor) with the desired value of speed setting by user (22). The result of this comparison is PWM (pulse width modulation) pulses with fixed frequency but variable duty cycle. Feedback pulses are taken from RPM sensor (23) mounted in the rear shaft of dc motor (16). Frequency of these pulses is proportional to RPM of dc motor. These pulses are shaped in mono stable multi vibrator (MMV). After integration of pulses by integrator a dc voltage is generated at TP1 in diagram that is equal to velocity of target, i.e. 1.00-8.00 volts for 1.00-8.00 cm/s. This dc signal is used to display velocity of target by three digit digital voltmeter (DVM) (24) in FIG. 8 and FIG. 9. This signal is then fed to non-inverting input of first operational amplifier (OP1) with unity gain arranged in form of instrumentation amplifier.

The set speed signal is also a variable dc voltage produced by set speed volume (22) in the range of 1.00-8.00 volts. This signal is fed to non-inverting input of OP1. The output signal of OP1 is fed to the inverting input of second operational amplifier OP2 arranged in form of comparator. A sawtooth signal with frequency of 100 Hz and maximum amplitude of 8 volts is fed to none inverting input of comparator OP2. The output signal of OP2 is PWM rectangular pulses with frequency of 100 Hz but variable duty cycle. This PWM signal derives the dc servo motor by a transistor driver.

The unit is switched on and off by switch (25) and the speed of target can set by speed volume (22). A twin cable (26) connects target velocity control unit (4) to target assembly (3). This cable (26) inters the target velocity control unit to connectors (27) and (28) in FIG. 9. at one end and inters to the target assembly (29) in FIG. 6. At the other end.

PARTS

1: Tank
2: X-Y positioning device
3—Target assembly
4: Target velocity control unit
5: Probe holder device
6: screws
7: O-ring robber
8: Y-Direction Knob
9: X-Direction Knob
10: Connector of control unit 9 and target assembly 3
11: Knob
12: DC motor
13: Shaft of DC motor
17: Pulleys (14) and (14)
18: Pins
19: screws
20: On/Off switch
21: velocity dial 25
24: 3 digit digital panel meter

The invention claimed is:

1. An Ultrasonography Doppler phantom evaluation system, comprising:
   a) A string phantom target comprising four independently adjustable parameters including target velocity, target angle, target depth and target lateral distance;
   b) A water tank;
   c) X-Y positioning device attached to said water tank; that moves said string phantom target in an X-Y coordinates;
   d) Target assembly which holds said string phantom target/moving target driven by a DC servo motor; and
   e) A target velocity control unit that controls a speed of said moving target driven by said DC servo motor, wherein a probe holder device is attached to an outer wall of said tank.

2. The device of claim 1, wherein said probe holder device is attached to said water tank in a direction perpendicular to a water level in said water tank.

3. The device of claim 2, wherein said probe holder holds an ultrasound probe.

4. The device of claim 3, wherein a location of said X-Y positioning device is adjusted in each of X and Y axis via two knobs respectively; and wherein said target assembly is attached to said X-Y positioning device.

5. The device of claim 4, wherein said target assembly comprises four pulleys (two sets), wherein one of said sets of pulleys rotates via a shaft of said DC motor with a controlled speed; wherein said four pulleys hold an O-ring shaped rubber of said moving target.

6. The device of claim 5, wherein said moving target rotates changing its angle with respect to the horizontal axis in 0-65 degrees; wherein an angle of said moving target is indicated by a scale on top of said target assembly and said moving target is fixedly tightened at a desired angle on said target assembly.

7. The device of claim 6, wherein said device further comprises markings and numbers on its walls so that said angle change of said moving target is indicated by said markings, and wherein said angle is fixed via a target fastening knob.

8. The device of claim 7, wherein said probe directs an ultrasound beam towards said moving string target immersed in said water tank.

9. The device of claim 8, wherein a depth of said moving target in said water tank is set and adjusted independent of said target angle.

10. The device of claim 9, wherein at least two pins attached to said pulleys and said moving target, prevents said moving target from vibration.

11. The device of claim 10, wherein said target velocity, said target angle, said target depth and said target lateral distance is adjusted independent from one another.

12. The device of claim 11, wherein said target lateral distance in relation to said ultrasound beam is altered and precisely aligned.

13. The device of claim 12, wherein said moving target is a rubber string that mimics a flow of blood inside a blood vessel.

14. The device of claim 13, wherein said rubber string moves in a closed loop quadratic track inside said water tank; wherein said moving rubber string simulates blood stream with known velocity and said water inside said water tank simulates stationary tissue surrounding said blood stream.

\* \* \* \* \*